(12) United States Patent
Nakashima et al.

(10) Patent No.: US 10,449,510 B2
(45) Date of Patent: Oct. 22, 2019

(54) AGENT FOR ADSORPTION OF RUTHENIUM FROM AQUEOUS SOLUTION AND METHOD FOR ADSORPTION OF RUTHENIUM FROM AQUEOUS SOLUTION

(71) Applicants: Clariant Catalysts (Japan) K.K., Tokyo (JP); Ebara Corporation, Tokyo (JP)

(72) Inventors: Tadahito Nakashima, Toyama (JP); Hyun-Joong Kim, Toyama (JP); Takashi Sakuma, Tokyo (JP); Makoto Komatsu, Tokyo (JP); Takeshi Izumi, Tokyo (JP)

(73) Assignees: Clariant Catalysts (Japan) K.K., Tokyo (JP); Ebara Corporation, Tokyo (JP)

( * ) Notice: Subject to any disclaimer, the term of this patent is extended or adjusted under 35 U.S.C. 154(b) by 43 days.

(21) Appl. No.: 15/560,348

(22) PCT Filed: Mar. 22, 2016

(86) PCT No.: PCT/JP2016/001635
§ 371 (c)(1),
(2) Date: Sep. 21, 2017

(87) PCT Pub. No.: WO2016/152141
PCT Pub. Date: Sep. 29, 2016

(65) Prior Publication Data
US 2018/0071712 A1    Mar. 15, 2018

(30) Foreign Application Priority Data

Mar. 24, 2015  (JP) ................................. 2015-060857

(51) Int. Cl.
*B01J 20/06*    (2006.01)
*C02F 1/28*    (2006.01)
(Continued)

(52) U.S. Cl.
CPC ........... *B01J 20/06* (2013.01); *B01J 20/2803* (2013.01); *B01J 20/28011* (2013.01); (Continued)

(58) Field of Classification Search
None
See application file for complete search history.

(56) References Cited

U.S. PATENT DOCUMENTS

| | | | | |
|---|---|---|---|---|
| 4,902,665 A * | 2/1990 | Elfline | ...................... | G21F 9/10 502/402 |
| 5,672,329 A * | 9/1997 | Okada | ................... | C01G 45/02 423/594.14 |
| 2005/0214199 A1 | 9/2005 | Hayashi et al. | | |

FOREIGN PATENT DOCUMENTS

JP    2009-254920 A    11/2009
JP    2010-58008 A    3/2010
(Continued)

OTHER PUBLICATIONS

Bo Tang et al., "Novel dandelion-like beta-manganese dioxide microstructures and their magnetic properties," 2006 Nanotechnology 17 pp. 947-951. (Year: 2006).*

(Continued)

*Primary Examiner* — Chester T Barry
(74) *Attorney, Agent, or Firm* — Scott R. Cox

(57) ABSTRACT

An adsorbent is provided to adsorb ruthenium from aqueous solution for recovery and/or reuse or removal of said ruthenium, and a method for purifying, for example, sea water and/or water containing sodium ions, magnesium ions, calcium ions, chlorine ions or other ions, polluted with a radioactive element, using said adsorbent.
The ruthenium adsorbent includes manganese in the form of oxides thereof. The adsorbent can further include at least one additional transition metal element other than manganese, such as copper. The adsorbent soaked in water removes
(Continued)

X-ray diffraction patterns radioactive ruthenium or the like through adsorption, and thereby can purify, for example, sea water and/or water containing sodium ions, magnesium ions, calcium ions, chlorine ions or other ions.

21 Claims, 5 Drawing Sheets

(51) Int. Cl.
| | |
|---|---|
| *C22B 11/00* | (2006.01) |
| *C01G 45/02* | (2006.01) |
| *B01J 20/28* | (2006.01) |
| *C01B 33/113* | (2006.01) |
| *C01F 7/02* | (2006.01) |
| *C01G 55/00* | (2006.01) |
| *C02F 101/00* | (2006.01) |
| *C02F 101/20* | (2006.01) |
| *G01N 23/20* | (2018.01) |

(52) U.S. Cl.
CPC ........ *B01J 20/28057* (2013.01); *C01G 45/02* (2013.01); *C02F 1/28* (2013.01); *C02F 1/281* (2013.01); *C22B 11/00* (2013.01); *C01B 33/113* (2013.01); *C01F 7/02* (2013.01); *C01G 55/00* (2013.01); *C02F 2101/006* (2013.01); *C02F 2101/20* (2013.01); *G01N 23/20075* (2013.01)

(56) References Cited

FOREIGN PATENT DOCUMENTS

| JP | 2010058008 A | * | 3/2010 |
|---|---|---|---|
| JP | 2011-045806 A | | 3/2011 |
| JP | 2011045806 A | * | 3/2011 |
| JP | 2012-41593 A | | 3/2012 |
| JP | 2013-95979 A | | 5/2013 |
| JP | 5339302 B2 | | 11/2013 |
| JP | 2014-43611 A | | 3/2014 |
| JP | 2014-77162 A | | 5/2014 |

OTHER PUBLICATIONS

Japan Atomic Energy Research Institute Report JAERI-M 9159.
Written Opinion of the International Searching Authority for International Application No. PCT/JP2016/001635 dated Jun. 21, 2016.
International Searching Authority for International Application No. PCT/JP2016/001635 dated Jun. 21, 2016.
International Preliminary Report on Patentability for International Application No. PCT/JP2016/001635 dated Jun. 21, 2016.
Extended European Search Report, including Supplementary European Search Report, with European Search Opinion, dated Nov. 19, 2018, for Relevant European Patent Application No. 16768048.7/ International Application No. PCT/JP2016/001635. English Translation Provided.
Database WPI, Week 201021, Thomson Scientific, London, GB; AN 2010-C93905, XP002785880; Mar. 18, 2010 Abstract.
Database WPI, Week 201120, Thomson Scientific, London, GB; AN 2011-C30600, XP002785881; Mar. 10, 2011 Abstract.
Husam H Al-Taweel: "Study of Optimum Conditions for the Removal of Ruthenium and Cerium Using Freshly Prepared Manganese Dioxide Introduction", IBN Al-Haitham Jour. for Pure & Appl. Sci.; vol. 26(1) 2013, pp. 218-224 (English Translation).
P. Guegueniat: "Determination of the ruthenium, cerium and zirconium radio-activity of sea-water by carrying-over and adsorption using manganese dioxide." CEA-R 3284; Jan. 1, 1967—Partial English translation of pp. 1 & 2.

* cited by examiner

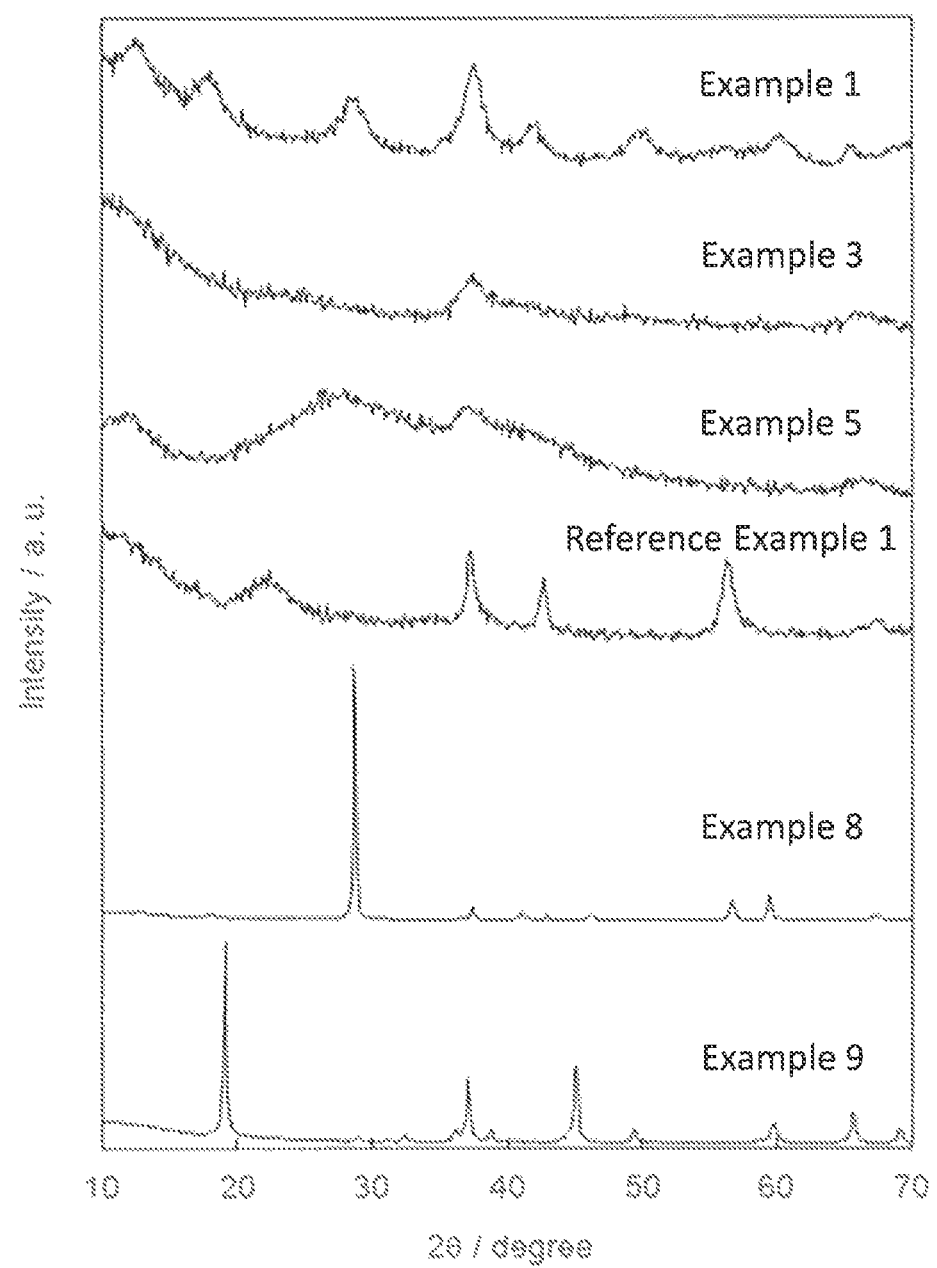
Figure 1: X-ray diffraction patterns

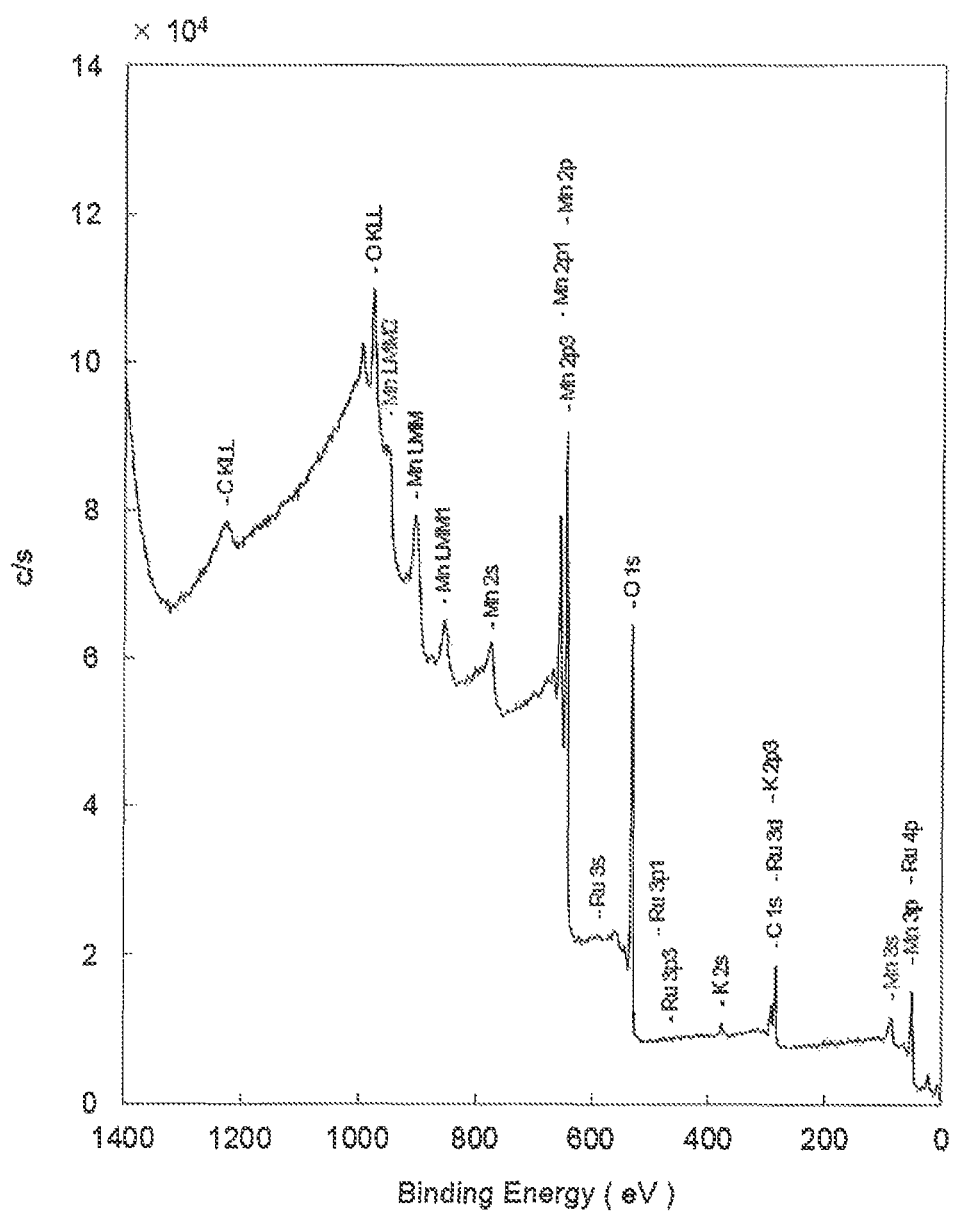
Figure 2: XPS wide spectrum for adsorbent B before ruthenium adsorption test

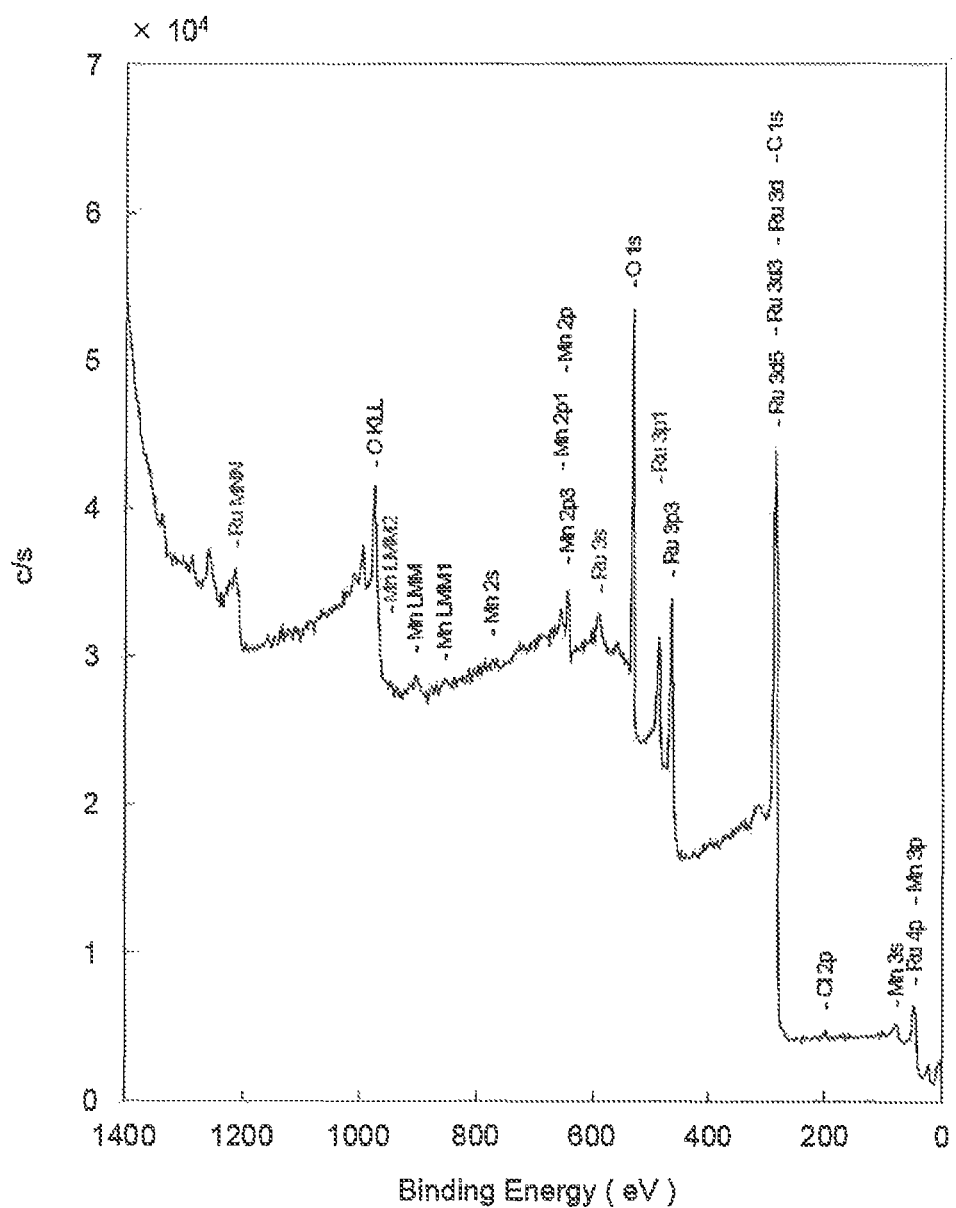
Figure 3: XPS wide spectrum for adsorbent B after ruthenium adsorption test

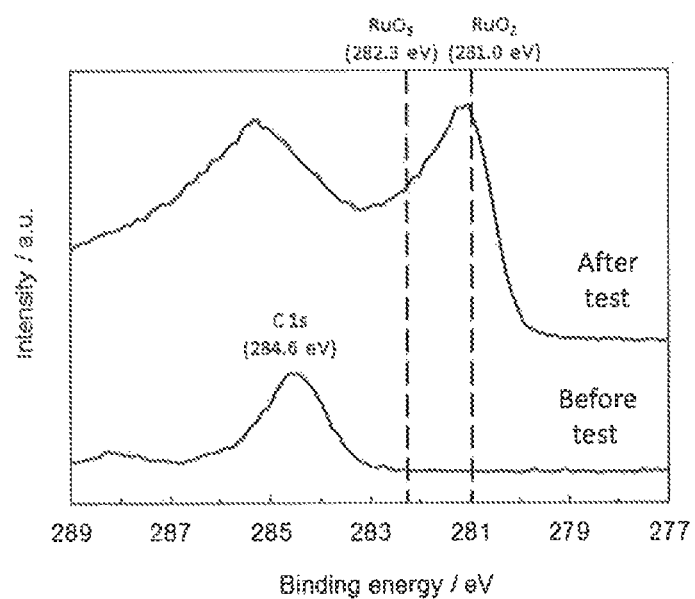
Figure 4: Ru 3d XPS spectra for adsorbent B before and after ruthenium adsorption test

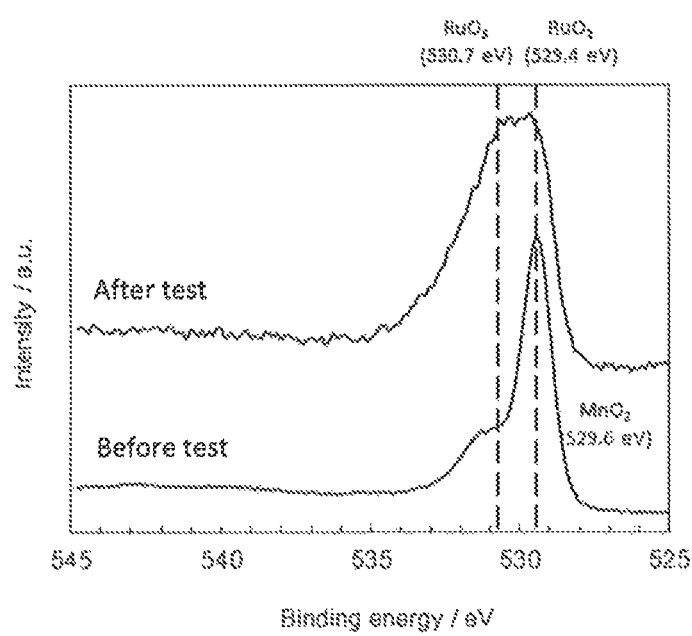
Figure 5: O 1s XPS spectra for adsorbent B before and after ruthenium adsorption test

AGENT FOR ADSORPTION OF RUTHENIUM FROM AQUEOUS SOLUTION AND METHOD FOR ADSORPTION OF RUTHENIUM FROM AQUEOUS SOLUTION

TECHNICAL FIELD

The present invention relates to an adsorbent for recovering (and/or reusing) or removing ruthenium from aqueous solution thereof by adsorbing the ruthenium in the aqueous solution, which includes any form of a ruthenium cation, a ruthenium complex ion and a ruthenate ion, on the adsorbent; and relates to a method for purifying sea water or the like polluted with a radioactive element, using said adsorbent.

BACKGROUND ART

In recent years, there has been an increase in demand for metal resources. Among them, demand for noble metals has also increased as noble metals are used in e.g. electronic devices and various catalysts although reserves of them are scarce and supplies are limited. Therefore, the need for them to be effectively used and recovered has increased. One noble metal, Ruthenium, has also been used for wider applications including as a material for hard disks and as a catalyst in the production of hydrogen, and it has become important to improve techniques for recovery of ruthenium from waste fluid resulting from the production of such products or from the metal-dissolving solution generated during the recycling of industrial products.

In addition, as it is considered that radioactive elements are discharged as a result of nuclear plant accidents through subterranean routes to pollute the ocean, the removal of such pollutants is now critical. The radioactive elements discharged include radioactive ruthenium, and removal of the radioactive ruthenium from soil or sea water and/or purification thereof is also critical.

In such situations, ruthenium is usually present as an ion in an aqueous solution thereof and the recovery of ruthenium from or purification of ruthenium-containing water requires selective adsorption or filtration of ruthenium, or a treating agent which selectively reacts with ruthenium. In particular, the removal of radioactive ruthenium from and/or purification of radioactive ruthenium-containing water requires an extremely high removal performance, a simple removal apparatus, and a safe and inexpensive adsorbent and/or treating agent.

Many methods for recovering and/or removing noble metals including ruthenium have been previously proposed. For example, Patent Literature 1 describes a method of heating a material, on which a noble metal such as rhodium, palladium and ruthenium are supported, to allow the noble metal to be absorbed into a material having a perovskite crystal structure. Although this method is preferable for the recovery of a useful metal from a catalyst used in the treatment of automobile exhaust gas, the method requires a heating process at 1000° C. or higher, and thus it is difficult to adapt said method to applications in which a noble metal ion present in water is recovered and/or removed from the water.

Patent Literature 2 shows a method of allowing a metal ion to be adsorbed on an ion exchange resin or a chelating resin in an aqueous solution. Such a method of absorbing a metal ion with an ion exchange resin or the like provides only a limited removal of ruthenium per volume of an adsorbent due to the small number of adsorption sites in the adsorbent. This drives the cost required for the adsorbent up, and thus, in cases where a large amount of ruthenium-containing water is treated, the cost for the adsorption treatment of ruthenium increases, compromising the economic desirability of such a situation.

Patent Literature 3 shows a method of removing radioactive palladium or radioactive ruthenium from aqueous solution thereof by using a metal ferrocyanide. Although this method is preferable in that the ions in the aqueous solution can be removed, the ferrocyanide may decompose at high temperatures, generating harmful hydrogen cyanide. In addition, the removal efficiency is not sufficiently high, and moreover, decomposition may be caused in aqueous solutions with a high pH, allowing adsorbed radioactive ruthenium to be released and resulting in a lower removal efficiency. This complicates the management of the adsorption treatment system, and necessitate the treatment of cyanide-containing waste water, for safety.

Particularly in cases where the target for removal is, for example, water used for washing soil polluted with a radioactive element or sea water polluted with a radioactive element, such a target usually has a low concentration of ruthenium and typically requires large scale treatment, and thus the removal of the radioactive elements requires an extremely high removal performance in a small quantity, and a reduction in cost. With regards to removal efficiencies, e.g. for radioactive elements including strontium scattered by the explosion of a nuclear reactor, the final removal efficiency after purification must be 99% or higher or 99.9% or higher, because of the seriousness of its impact.

Another significant problem in the treatment of waste water from a nuclear reactor is the possible presence of ruthenium in various structures. As shown in Non Patent Literature 1, the structure of ruthenium is believed to change depending on the type of aqueous solution with which it has come into contact during nuclear fission from radioactive uranium. Ruthenium may be present in various structures depending on conditions such as the temperature of the aqueous solution thereof and chemical species dissolved therein, and a high removal performance is required for respective structures.

It is considered that a removal efficiency similar or comparable to that for radioactive strontium is necessary for radioactive ruthenium. Even assuming that the removal efficiency is 60% per cycle of treatment, 40% is discharged, and, for the removal of at least 99%, five or more cycles of treatment must be performed; however, this is significantly inefficient for applications in which a large amount of polluted water is treated. If a material which provides a removal efficiency of 95% or higher can be obtained, the discharge ratio after one cycle of treatment is at most 5%, and a removal efficiency of 99.75% or higher can be achieved in two cycles of treatment. Even in cases where a secondary treatment facility with e.g. a reverse osmosis membrane is provided downstream of the primary treatment with an adsorbent, the achievement of a high removal efficiency of, for example, 95% or higher at the primary treatment stage will significantly reduce the load applied to the step of the expensive secondary treatment, and this situation is very preferable in terms of cost-efficiency. Accordingly, this will require an adsorbent having a removal efficiency of 95% or higher for ruthenium cations which are expected to exist at a particularly high content, and having a removal efficiency comparable thereto for other ion species such as ruthenium complex ions and ruthenate ions.

Such an adsorbent needs to be capable of treating a large amount of water, and therefore needs to have sufficient stability for extensive treatment. For such a material, water-insoluble materials such as metal oxides are preferred.

In terms of safety, the use of an adsorbent or treating agent which induces environmental pollution is not preferable. Raw materials to be used need to be inexpensive, and moreover it is not preferable that their production involves the volatilization of an organic solvent, or the consumption of a massive amount of energy such as calcination at high temperature, and the process used to produce such materials should be simple.

As described above, although there is a high demand for the replacement of conventional methods for removing or recovering ruthenium by a simple and safe method using an inexpensive adsorbent or treating agent with a high removal efficiency, an adsorbent or treating agent satisfying performance requirements including 1) ability to remove various ion species and further 2) a high removal efficiency of 70% or higher, preferably 95% or higher, for ruthenium cations, as well as safety and low cost, has not yet been obtained.

CITATION LIST

Patent Literature

Patent Literature 1: JP5339302B2
Patent Literature 2: JP2013-95979A
Patent Literature 3: JP2014-77162A
Non Patent Literature 1: Japan Atomic Energy Research Institute Report JAERI-M 9159

SUMMARY OF INVENTION

Technical Problem

A primary object of the present invention is to provide a material capable of adsorbing ruthenium cations in an aqueous solution, and additionally capable of adsorbing ruthenium complex ions and ruthenate ions, without any complicated apparatus or energy such as high temperature.

A further object of the present invention Is to provide a material capable of adsorbing ruthenium cations in an aqueous solution with a high efficiency of 70% or more, or even 95% or more, and additionally capable of adsorbing ruthenium complex ions and ruthenate ions, without any complicated apparatus or energy such as high temperature.

Another object of the present invention is to provide an adsorbent for ruthenium in an aqueous solution, which enables an inexpensive, safe and simple treatment, by using as the adsorbent metal oxides which are inexpensive and less likely to cause environmental pollution.

Another object of the present invention is to provide a method enabling the adsorption of ruthenium ions in a simple and safe manner by merely soaking a material in aqueous solution containing ruthenium.

Still another object of the present invention is to provide a method for adsorbing and removing radioactive ruthenium from water discharged from a nuclear reactor or the like to purify the water.

Other objects of the present invention will become apparent from the following description.

Solution to Problem

In view of the circumstances described above, the present inventors conducted extensive research to solve the drawbacks of the conventional technique, and discovered the following findings and guidelines as an idea to achieve the objects of the present invention.

(1) The present inventors searched for a material capable of adsorbing ruthenium present in aqueous solution thereof primarily from metal oxides which are chemically stable and less likely to cause environmental pollution, and found that manganese oxides adsorb ruthenium.

(2) In particular, a high ruthenium removal efficiency (e.g. a ruthenium removal efficiency of 70% or more) can be achieved in the case of manganese oxides having an appropriate surface area, and thus the specific surface area of the manganese oxides is preferably 70 $m^2/g$ or more.

(3) Although an adsorbent only with manganese oxides can provide higher adsorbing performance than conventional adsorbents, it proved difficult to achieve a ruthenium removal efficiency of 90% or more, preferably 95% or more.

(4) In view of this, the present inventors examined methods in which a metal compound other than manganese is added to allow the metal compound to coexist with the manganese, and found that the addition of a particular kind of metal significantly enhances the ruthenium removal efficiency.

(5) It was found that the metal element to be added is preferably a transition metal, especially iron, copper, cobalt and zinc are preferred, and copper is particularly preferred.

(6) It was also found that a high ruthenium removal efficiency can be achieved in cases where a manganese oxide is amorphous or has a layered structure or a tunnel structure in which at least two linked $MnO_6$ octahedrons form each horizontal and vertical side of the tunnel.

(7) The adsorbent is usually produced as a powder, but, as the powder may be scattered when handled, complicating the handling of the material, said powder should preferably be formed into a granule or the like. However, this reduces the effective surface area, thereby likely lowering the ruthenium removal efficiency. As a method for preventing such lowering in removal efficiency, the present inventors found that mixing the adsorbent powder with, for example, a aluminum oxide powder followed by forming the powder into a shaped article can prevent the aforementioned reduction in specific surface area, and thus can maintain a high ruthenium removal efficiency. This was inferred to be an effect of the porous nature of aluminum oxide to bind the adsorbent powder thereon without interfering with the adsorption of ruthenium.

(8) Although it is unclear why the combination of appropriate specific surface area, an amorphous or appropriate structure and a particular transition metal element described above is responsible for the resulting high ruthenium removal efficiency of 95% or higher, as one possible reason for the result, the present inventors inferred that said combination results in an increase in the number of adsorption sites for ruthenium, and furthermore, that ruthenium Is strongly adsorbed in association with chemical reaction, and adsorbed ruthenium is thus less likely to be detached.

(9) When the adsorbent thus obtained was tested using ruthenium ion-containing water, a high ruthenium removal efficiency of 70% or more, preferably 95% or more, was achieved, and, in addition, the adsorbent adsorbed ruthenium complex ions and ruthenate ions, and thus the present inventors achieved the present invention.

(10) It was found that, in the case of using manganese oxides for the adsorption treatment of aqueous solutions of ruthenium (III) having trivalent ruthenium, the ruthenium became tetravalent or higher-valent after being adsorbed on the manganese oxides. From this result, the present inventors inferred that the manganese oxide-based adsorbent strongly adsorbs ruthenium through oxidation of ruthenium, and this strong adsorption is one reason for the high ruthenium removal efficiency.

Specifically, the present invention relates to the following:
1. A ruthenium adsorbent for adsorbing ruthenium from aqueous solution thereof, said adsorbent comprising manganese oxides as a primary component.
2. The adsorbent according to the above 1, wherein $MnO_2$ consisting of $\varepsilon$-$MnO_2$ and/or $\gamma$-$MnO_2$ is excluded from the manganese oxides.
3. The adsorbent according to the above 1 or 2, wherein the aqueous solution comprises ruthenium in the form of a ruthenium cation, a ruthenium complex ion and/or a ruthenate ion.
4. The adsorbent according to any one of the above 1 to 3, wherein the manganese oxides have an amorphous structure and/or a layered structure and/or a tunnel structure.
5. The adsorbent according to any one of the above 1 to 4, wherein, in the case that the manganese oxides have a tunnel structure, the adsorbent comprises oxides of manganese having at least two linked $MnO_6$ octahedrons forming each horizontal and vertical side of the tunnel.
6. The adsorbent according to any one of the above 1 to 4, wherein the manganese oxides have an amorphous structure and/or $\alpha$-$MnO_2$ and/or $\delta$-$MnO_2$.
7. The adsorbent according to any one of the above 1 to 6, wherein the manganese oxides have an amorphous structure and/or $\alpha$-$MnO_2$, and the aqueous solution comprises ruthenium in the form of a ruthenium cation.
8. The adsorbent according to any one of the above 1 to 7, wherein the content of manganese calculated as manganese dioxide is 50 parts by weight or more, based on 100 parts by weight of the adsorbent.
9. The adsorbent according to any one of the above 1 to 8, further comprising at least one additional transition metal elements other than manganese.
10. The adsorbent according to the above 9, wherein the transition metal element is in the form of oxides thereof.
11. The adsorbent according to the above 10, wherein manganese and the transition metal element are present in the form of a physical mixture of manganese oxides and oxides of the transition metal element.
12. The adsorbent according to the above 10, wherein manganese and the transition metal element are present in the form of composite oxides thereof.
13. The adsorbent according to the above 11, wherein the weight ratio of manganese oxides to transition metal oxides is 1:0.001 to 1:1, when the weight of the manganese oxides are calculated as the weight of manganese dioxide.
14. The adsorbent according to the above 12, wherein the molar ratio of manganese to transition metal element is 1:0.001 to 1:1.
15. The adsorbent according to any one of the above 9 to 14, wherein the transition metal element is selected from the group consisting of iron, cobalt, copper and zinc.
16. The adsorbent according to any one of the above 1 to 15, having a specific surface area of 70 to 700 $m^2/g$.
17. The adsorbent according to any one of the above 1 to 16, in the form of a powder.
18. The adsorbent according to any one of the above 1 to 16, in the form of a shaped article.
19. The adsorbent according to any one of the above 1 to 18, comprising an inorganic binder which comprises a metal element other than transition metals and/or a metalloid element.
20. The adsorbent according to the above 19, wherein the inorganic binder is aluminum oxides or silicon oxides.
21. Use of the adsorbent according to any one of the above 1 to 20, for removing radioactive ruthenium in water through adsorption.
22. Use of the adsorbent according to any one of the above 1 to 20, for recovering ruthenium from waste fluid discharged from a production line for industrial products and/or a recycling process for industrial products.
23. A method for removing radioactive ruthenium from radioactive ruthenium-containing water, comprising contacting the radioactive ruthenium-containing water with the adsorbent according to any one of the above 1 to 20.
24. A method for removing ruthenium from ruthenium-containing water, comprising contacting the water with the adsorbent according to any one of the above 1 to 20 to oxidize ruthenium, provided that ruthenate ion-containing water is excluded from the ruthenium-containing water.
25. The method according to the above 23 or 24, wherein the water is sea water and/or water containing a sodium ion, a magnesium ion, a calcium ion, a chlorine ion and/or other ions, polluted with a radioactive element, including radioactive ruthenium.

In further embodiments of the present invention, the present invention relates to the following:
1. A ruthenium adsorbent for adsorbing ruthenium (Ru) ions from aqueous solution of ruthenium, said adsorbent comprising manganese in the form of oxides thereof.
2. The adsorbent according to the above 1, wherein the content of the manganese in the form of oxides thereof, calculated as manganese dioxide, is 50 parts by weight or more based on 100 parts by weight of the adsorbent.
3. The adsorbent according to the above 1 or 2, wherein the manganese in the form of oxides thereof is present exclusively as manganese oxides.
4. The adsorbent according to the above 1 or 2, further comprising at least one additional transition metal elements other than manganese.
5. The adsorbent according to the above 4, the transition metal element is in the form of oxides thereof.
6. The adsorbent according to the above 5, wherein manganese and the transition metal element are present in the form of a physical mixture of manganese oxides and transition metal element oxides.
7. The adsorbent according to the above 5, wherein manganese and the transition metal element are present in the form of composite oxides thereof.
8. The adsorbent according to the above 6, wherein the weight ratio of manganese oxides to oxides of the transition metal is 1:0.001 to 1:1, when the weight of the manganese oxides is calculated as the weight of manganese dioxide.
9. The adsorbent according to the above 7, wherein the molar ratio of manganese to transition metal element is 1:0.001 to 1:1.
10. The adsorbent according to any one of the above 4 to 9, wherein the transition metal element is selected from the group consisting of iron, cobalt, copper and zinc.
11. The adsorbent according to any one of the above 1 to 10, having a specific surface area of 70 to 700 $m^2/g$.
12. The adsorbent according to any one of the above 1 to 11, in the form of a powder.
13. The adsorbent according to any one of the above 1 to 11, in the form of a shaped article.
14. The adsorbent according to any one of the above 1 to 13, comprising an inorganic binder which comprises a metal element other than transition metals and/or a metalloid element.
15. The adsorbent according to the above 14, wherein the inorganic binder is aluminum oxides or silicon oxides.

16. Use of the adsorbent according to any one of the above 1 to 15 for removing radioactive Ru ions in water through adsorption.
17. Use of the adsorbent according to any one of the above 1 to 15 for recovering Ru ions from waste fluid discharged from a production line for industrial products and/or a recycling process for industrial products.
18. A method for removing radioactive Ru ions from radioactive Ru ion-containing water, comprising contacting the radioactive Ru ions-containing water with the adsorbent according to any one of the above 1 to 15.
19. The method according to the above 18, wherein the water is sea water polluted with a radioactive element including a radioactive Ru ion.
20. The adsorbent according to any one of the above 1 to 15, for removing radioactive Ru ions in water through adsorption.
21. The adsorbent according to any one of the above 1 to 15, for recovering Ru ions from waste fluid discharged from a production line for industrial products and/or a recycling process for industrial products.

Advantageous Effects of Invention

As is clear from the above description, the present invention can provide an adsorbent having high adsorbing performance, preferably with a removal efficiency of 70% or more, more preferably with a removal efficiency of 95% or more, for ruthenium in aqueous solution. By utilising the high removal efficiency, recovery of ruthenium from industrial waste water or from a recycling process, removal of radioactive ruthenium from groundwater or sea water polluted with radioactive ruthenium, and purification of said groundwater or sea water can be performed in a safe and economical manner without the need for any expensive apparatus.

BRIEF DESCRIPTION OF DRAWINGS

FIG. 1 shows XRD patterns for adsorbents demonstrated in Examples 1, 3 and 5, Reference Example 1 and Examples 8 and 9.
FIG. 2 shows an XPS wide spectrum for an adsorbent demonstrated in Example 2 before a ruthenium adsorption test.
FIG. 3 shows an XPS wide spectrum for an adsorbent demonstrated in Example 2 after a ruthenium adsorption test.
FIG. 4 shows Ru 3d XPS spectra for an adsorbent demonstrated in Example 2 before and after a ruthenium adsorption test.
FIG. 5 shows O 1s XPS spectra for an adsorbent demonstrated in Example 2 before and after a ruthenium adsorption test.

DESCRIPTION OF EMBODIMENTS

Specifically, the present invention is an adsorbent for ruthenium in an aqueous solution, the adsorbent comprising manganese oxides, and a method for removing ruthenium from ruthenium-containing water, for example, from sea water containing radioactive ruthenium, using said adsorbent.
The forms of ruthenium in its aqueous solution to be adsorbed by the adsorbent according to the present invention include a ruthenium cation, a ruthenium complex ion and a ruthenate ion.

The adsorbent according to the present invention is based on manganese oxides.
As described above, the present invention is based on the discovery that manganese oxides have ruthenium-adsorbing properties.
In an embodiment of the present invention, the content of manganese in the adsorbent according to the present invention, calculated as manganese dioxide, can be 50 parts by weight or more, for example, 60 parts by weight or more, 70 parts by weight or more, 80 parts by weight or more, 90 parts by weight or more, or 95 parts by weight or more, based on 100 parts by weight of the adsorbent. For example, the adsorbent according to the present invention can comprise manganese in an amount, in terms of manganese dioxide, of 50 parts by weight to 100 parts by weight based on 100 parts by weight of the adsorbent. In cases where the amount of manganese is 100 parts by weight, the adsorbent according to the present invention consists only of manganese dioxide.
In an embodiment of the present invention, the adsorbent according to the present invention can further contain at least one additional transition metal elements other than manganese.
In the present specification, it was also found that the at least one additional transition metal element contained in the adsorbent according to the present invention enhances the ruthenium removal efficiency of the adsorbent. Examples of said transition metal element include copper, iron, cobalt and zinc, among which copper is particularly preferably used; use of copper can particularly significantly enhance the ruthenium removal efficiency.
The transition metal element can be, for example, in the form of an oxide thereof. In this case, manganese and the transition metal element can be present in the form of a physical mixture of manganese oxides and transition metal element oxides. In the case that the transition metal element is copper, for example, manganese and copper can be present in the form of a physical mixture of manganese oxides and copper oxides. In this way, coexistence of the additional transition metal in the form of oxides and manganese oxides in the adsorbent as a result of the mixing of the manganese oxides with the oxides of the additional transition metal is preferable in terms of chemical stability, ruthenium removal efficiency, cost, etc.
Alternatively, the transition metal element can be present as composite oxides with manganese. This embodiment, in which the transition metal element is present in the form of composite oxides with manganese in the adsorbent, is also preferable in terms of chemical stability, ruthenium removal efficiency, cost, etc. In the case that the transition metal element is copper, for example, the adsorbent according to the present invention comprises composite oxides of manganese and copper.
Moreover, the adsorbent according to the present invention can comprise both a physical mixture of manganese oxides and the transition metal element oxides, and composite oxides of manganese and the transition metal. In summary, in the adsorbent according to the present invention, manganese and the transition metal element can be present in the form of a physical mixture of manganese oxides and transition metal element oxides, or in the form of composite oxides of manganese and the transition metal element, or in both of the forms.
Here, "physical mixture" refers to a mixture of two or more single oxides and/or composite oxides.
"Composite oxide" refers to an oxide in which two or more atoms other than oxygen are present in a single structure, and, for example, a composite oxide of manganese and copper is an oxide containing manganese and copper in a single structure.

In the case that the adsorbent according to the present invention comprises at least one additional transition metal element other than manganese, and manganese and said transition metal element are present in the form of a physical mixture of manganese oxides and oxides of the transition metal element, the ratio (weight ratio) of manganese oxides to additional transition metal element oxides (in the case that two or more transition metal elements are contained, oxides of all of them) depends on the type of the transition metal element, and can be 1:0 to 1:1.0, for example, 1:0.001 to 1:1, preferably 1:0.01 to 1:0.5, for example, 1:0.05 to 1:0.5, or 1:0.1 to 1:0.4, when the weight of manganese oxide is calculated as that of manganese dioxide and the weight of the transition metal element is calculated as that of a stable oxide of the metal (e.g. copper oxide (CuO) for copper, iron oxide ($Fe_2O_3$) for iron). From the viewpoint of prevention of the lowering of the ruthenium removal efficiency, the weight ratio is preferably in these ranges.

In cases where the adsorbent according to the present invention comprises at least one additional transition metal element other than manganese, and manganese and the transition metal element are present in the form of composite oxides, the molar ratio of manganese to transition metal element can be 1:0 to 1:1.0, for example, 1:0.001 to 1:1, preferably 1:0.01 to 1:0.5, for example, 1:0.05 to 1:0.5, or 1:0.1 to 1:0.4. From the viewpoint of prevention of the lowering of the ruthenium removal efficiency, the molar ratio is preferably in these ranges.

For example, in cases where the transition metal element is copper and the adsorbent according to the present invention comprises a physical mixture of manganese oxides and copper oxides, the weight ratio of manganese oxides to copper oxides (where the respective weights are calculated as those of $MnO_2$ and CuO) can be $MnO_2$:CuO=1:0 to 1:1, for example, 1:0.001 to 1:1. From the viewpoint of prevention of the lowering of the ruthenium removal efficiency, the weight ratio is preferably in these ranges. In particular, the weight ratio is preferably $MnO_2$:CuO=1:0.01 to 1:0.5, for example, 1:0.05 to 1:0.5, more preferably $MnO_2$:CuO=1:0.1 to 1:0.4.

For example, in cases where the transition metal element is copper and the adsorbent according to the present invention comprises composite oxides of manganese and copper, the molar ratio of manganese to copper can be 1:0 to 1:1.1, for example, 1:0.001 to 1:1. From the viewpoint of prevention of the lowering of the ruthenium removal efficiency, the molar ratio is preferably in these ranges. In particular, the molar ratio is preferably Mn:Cu=1:0.01 to 1:0.5, for example, 1:0.05 to 1:0.5, more preferably Mn:Cu=1:0.1 to 1:0.4.

The quantity of manganese oxides, the weight ratio of manganese oxides to additional transition metal oxides, and the molar ratio of manganese to additional transition metal element in a composite oxide can be determined, for example, by measuring the quantities of manganese and the additional transition metal (e.g. copper) in the adsorbent by using a high-frequency inductively coupled plasma emission spectrometer, and then appropriately converting the obtained quantities to those of manganese dioxide and the transition metal oxide (e.g. CuO), or converting to moles.

The adsorbent according to the present invention can have a specific surface area of, for example, 70 to 700 $m^2/g$. A specific surface area of 70 $m^2/g$ or more allows the achievement of a satisfactory ruthenium removal efficiency, and a specific surface area of 700 $m^2/g$ or less can prevent rapid adsorption which may cause heat generation or the boiling of water on contacting with water, and thus the specific surface area is preferably in the above range. If such heat generation or the boiling of water occurs, in particular in the case that a granular, shaped article is used as the adsorbent, foaming takes place, collapsing the article, and the passing amount of water to be purified and the ruthenium removal efficiency are lowered. Installation of a cooler or the like to prevent such lowering involves economically undesirable side effects including increases in the cost of equipment and energy consumption. The specific surface area is more preferably in the range of 100 to 500 $m^2/g$, for example, 125 to 450 $m^2/g$, and particularly preferably in the range of 150 to 400 $m^2/g$.

The specific surface area can be measured through specific surface area measurement with nitrogen adsorption (BET method).

In the present invention, it was found that, in the case that the manganese oxides contained in the adsorbent have a particular structure, such as being amorphous, or having $\alpha$-$MnO_2$ with a tunnel structure, or $\delta$-$MnO_2$ with a layered structure, a further satisfactory ruthenium removal efficiency can be achieved, and that, in contrast, the ruthenium removal efficiencies for cases using $\beta$-$MnO_2$ with a tunnel structure and $\lambda$-$MnO_8$ with a spinel structure are lower than those using $\alpha$-$MnO_2$ and of $\delta$-$MnO_2$ with a layered structure.

Manganese oxide having a tunnel structure is classified with (m×n), where m is the number of linked $MnO_6$ octahedrons forming the horizontal side of the tunnel, and n is that of those forming the vertical side of the tunnel. $\alpha$-$MnO_2$ is classified as (2×2), $\beta$-$MnO_2$ as (1×1), and $\gamma$-$MnO_2$ as coexistence of (1×1) and (1×2). $\epsilon$-$MnO_2$ has a structure similar to that of $\gamma$-$MnO_2$, and includes microtwinning and many structural defects.

Accordingly, in an embodiment of the present invention, the adsorbent according to the present invention comprises manganese oxides being amorphous or having a layered structure or a tunnel structure in which at least two linked $MnO_6$ octahedrons form each horizontal and vertical side of the tunnel.

The structure can be confirmed from an XRD spectrum obtained in X-ray diffraction measurement with Cu-K$\alpha$ radiation.

One reason why the structure described above is preferable, which is still under speculation, is that the number of adsorption sites for ruthenium is larger, and sites at which adsorbed ruthenium is less likely to be detached are formed.

The adsorbent according to the present invention has the feature of oxidizing adsorbed ruthenium. The electronic state of the adsorbed ruthenium can be confirmed from an XPS spectrum obtained in X-ray photoelectron spectroscopy.

The manganese oxides or composite oxides of manganese and the additional transition metal element in the present invention can be prepared, for example, as follows.

A manganese oxide in the present invention can be obtained, for example, by making an aqueous solution of manganese sulfate alkaline (e.g. by mixing the solution with an aqueous solution of an alkaline compound such as sodium hydroxide, potassium carbonate and potassium hydroxide), and carrying out an oxidation treatment of the solution with potassium permanganate to form a precipitate, followed by filtering, washing and drying of the precipitate.

A composite oxide of manganese and the additional transition metal element in the present invention can be obtained, for example, by using a method of mixing a manganese compound and a compound of the additional transition metal together to obtain an oxide thereof.

In this method, for example, an aqueous solution containing a manganese compound and a compound of the additional transition metal is prepared, and an alkaline aqueous solution (e.g. an aqueous solution of an alkaline compound such as sodium hydroxide, potassium carbonate and potassium hydroxide) and potassium permanganate are added to the aqueous solution, and the resulting precipitate is filtered, washed and dried, and thus a composite oxide of manganese and the additional transition metal element can be obtained.

In cases where the transition metal element is copper, for example, as demonstrated later in Examples, a composite oxide of manganese and copper can be obtained through oxidation of manganese sulfate and copper sulfate in an aqueous solution thereof, by means of e.g. potassium permanganate, followed by washing and drying of resulting precipitate.

The specific surface area can be adjusted, for example, by appropriately changing the drying temperature. In the case of composite oxides, the molar ratio of manganese to additional transition metal element can be adjusted by appropriately changing the quantities of the raw materials so that the desired ratio is achieved.

A physical mixture of manganese oxides and additional transition metal oxides in the present invention can be prepared by mixing manganese oxides prepared as described above with oxides of the additional transition metal separately obtained or produced, or by, for example, weighing and homogeneously mixing predetermined quantities of the both powders.

The shape of the adsorbent according to the present invention is not limited. For example, the adsorbent can be used in the form of a powder. Nevertheless, the adsorbent is preferably formed into a certain shape to reduce the scattering of powder from the adsorbent, to allow an aqueous solution to easily pass through the adsorbent, to reduce pressure drop in filtration, or to mix the adsorbent homogeneously in the aqueous solution. For example, the shape can be in the form of a granule, pellet, cylindrical shaped article or the like, having a particle size of about 0.1 mm to 10 mm, more preferably, having a particle size of about 0.2 to 7 mm.

A shaped article, such as a granule, a pellet and a cylindrical shaped article, can be produced by using a known forming method. In the production of a granule, for example, the adsorbent in powder form is tightly pressed by using a high-pressure molding machine and then pulverized, and thus the adsorbent in the form of a granule can be obtained. In this case, the size of the granule can be appropriately adjusted through adjustment of the mesh size of a sieve.

The particle size of the shaped article can be measured by using a particle size measurement method with an analytical sieve (in accordance with "Test methods for sieving of chemical products" in JIS K0069).

In cases where the adsorbent according to the present invention is formed into a shaped article, for example, the adsorbent powder described above can be directly formed, or mixed with a binder (binding agent) and then formed. When the adsorbent powder is directly formed/granulated, the surface area decreases, and as a result the adsorption activity is likely to also decrease. Contrarily, it was found that the decrease in adsorption activity can be reduced when the aforementioned powder is mixed with a certain metal oxide and/or metalloid oxide, and then formed in a shaped article. Accordingly, in the production of a shaped article, it is preferable to form the powder into a shaped article after mixing the powder with a binder. Oxides of aluminum, silicon and the like, and oxides containing both aluminum and silicon such as zeolite have the large effect of preventing a decrease in said activity, and are thus preferable for the binder. In the present invention, aluminum oxide is particularly preferable.

Accordingly, in an embodiment of the present invention, the adsorbent according to the present invention can further comprise a binder, preferably an inorganic binder containing a metal element other than transition metals and/or a metalloid element. Here, "metalloid element" refers to an element of intermediate nature between metal and non-metal, and examples thereof include silicon, boron, germanium, arsenic, tin, tellurium and polonium.

In cases where the adsorbent according to the present invention comprises a binder, the weight ratio of manganese oxides (or a mixture of manganese oxides and oxides of the additional transition metal) to binder is 1:0 to 1:1, more preferably 1:0.01 to 1.0.7, even more preferably 1:0.03 to 1:0.3, for example, 1:0.05 to 1:0.2 (manganese oxides (or a mixture of manganese oxides and oxides of the additional transition metal):binder).

The adsorbent according to the present invention can comprise, as necessary and in addition to manganese oxides (or a mixture of manganese oxides and oxides of the additional transition metal) and the binder, any other components which do not impair the advantageous effects of the present invention.

Alternatively, in an embodiment of the present invention, the adsorbent according to the present invention can consist only of manganese oxides (or a mixture of manganese oxides and oxides of the additional transition metal) and the binder.

It is also preferable to use the adsorbent according to the present invention which is supported on a carrier. Examples of such carriers include, but are not limited to, nonwoven fabrics, papers, plastic sheets, and ceramic sheets. Among them, flexible materials, particularly nonwoven fabrics, are preferable. Use of a flexible carrier provides good handleability in use, and allows its use as a roll, and thus the throughput per unit volume can be enhanced. The nonwoven fabric material may be any water-insoluble material, and examples thereof include cellulose fibers, polyester fibers and polyamide fibers. To load the adsorbent on such a carrier, a method commonly used for loading various materials on various carriers can be appropriately used. For example, to load the adsorbent according to the present invention on the nonwoven fabric sheet obtained by tangling fibers, a method of bonding the adsorbent in powder form or the adsorbent formed into granules to the nonwoven fabric with an adhesive, or a method of coating the nonwoven fabric with the adsorbent together with a binder or the like can be used.

As described above, the adsorbent according to the present invention can adsorb ruthenium present in an aqueous solution thereof at a high removal efficiency.

Accordingly, in an embodiment of the present invention, the present invention relates to the use of an adsorbent comprising manganese in the form of its oxides to remove ruthenium from an aqueous solution thereof.

Furthermore, with the use of the adsorbent according to the present invention, ruthenium can be removed from ruthenium-containing water by allowing the adsorbent to adsorb ruthenium in the aqueous solution, and then optionally separating the adsorbent from the water treated with the adsorbent using a suitable known method.

In this case, the ruthenium-containing water is contacted with the adsorbent according to the present invention for adsorption of the ruthenium present in its aqueous solution on the adsorbent.

Accordingly, in an embodiment of the present invention, the present invention relates to a method for removing radioactive ruthenium from ruthenium-containing water, e.g. radioactive ruthenium-containing water, comprising contacting the ruthenium-containing water, for example, the radioactive ruthenium-containing water, with the adsorbent according to the present invention. Through this method, the water can be purified.

The method can further include separating the adsorbent having ruthenium adsorbed thereon from the water treated with the adsorbent.

The aqueous solution to be treated with the adsorbent according to the present invention may be any aqueous solution containing ruthenium, and examples thereof include waste fluid discharged from the production of industrial products and/or the recycling process of industrial products, sea water polluted with a radioactive element, and water containing sodium ions, magnesium Ions, calcium ions, chlorine ions and/or other ions and polluted with a radioactive element.

Examples of applicable methods for contacting the adsorbent according to the present invention with ruthenium-containing water include soaking the adsorbent in ruthenium-containing water, for example, in which the adsorbent charged in a stand-alone tank is soaked in ruthenium-containing water, and continuously feeding ruthenium-containing water into piping, a container or a tank filled with the adsorbent using piping for feeding said water, connected to said piping, container or tank. A plurality of treatment tanks with the adsorbent according to the present invention may be connected together, and, for example, an ion exchange resin column may be connected downstream of the treatment tank with the adsorbent. A device for the measurement/detection of metal ion concentration can be provided in the vicinity of the adsorbent in each part to properly manage, e.g. the replacement of the adsorbent.

Ruthenium-containing water can be appropriately pretreated, for example, treated with an ion exchange resin or chelating resin, before being contacted with the adsorbent according to the present invention.

By using the adsorbent according to the present invention, a removal efficiency for ruthenium cations of, for example, 70% or more, preferably 80% or more, more preferably 90% or more, particularly preferably 95% or more, can be achieved.

The adsorbent with metals such as ruthenium adsorbed thereon can be recovered or reused, optionally through separation from the treated water by using a suitable known method, followed by detachment of the metals by treatment with a treating agent suitable for the metals as adsorbed species, such as an acid and an alkali, and, as necessary, concentration. Further optionally, the adsorbent with metals adsorbed thereon can be directly solidified with cement or the like and discarded.

Hereinafter, the present invention will be described with reference to Examples. However, the present invention is in no way limited to these Examples.

EXAMPLES

Structural analysis and performance evaluation for adsorbents used in the following Examples, Comparative Examples and Reference Examples were performed according to the following methods.

(1) Specific surface area of adsorbent: Specific surface area measurement with nitrogen adsorption (BET method) was used. The apparatus used was Macsorb Model-1210 from MOUNTECH Co., Ltd.

(2) X-ray diffraction: Measurement was performed by using powder X-ray diffractometry with X'Pert PRO MPD from Spectris Co., Ltd.

(3) X-ray photoelectron spectroscopy (XPS). Measurement was performed by using PHI Quantum2000 from ULVAC-PHI, Inc. In the measurement, an aluminium anode was used.

(4) Measurement of ruthenium removal efficiency: To quantify the ruthenium concentration, a high-frequency inductively coupled plasma (ICP) emission spectrometer (from SHIMADZU Corporation, ICPS-8100) was used. Based on the values obtained, the ruthenium removal efficiency was calculated by using the following formula.

Ruthenium removal efficiency (%)=(ruthenium concentration in test solution before treatment−ruthenium concentration in test solution after treatment)/(ruthenium concentration in test solution before treatment)(×100)

Example 1

Preparation of Adsorbent A

The method for preparing adsorbent A was as follows: 700 g of manganese sulfate tetrahydrate was dissolved in 10,000 g of ion-exchanged water; to this aqueous solution, a mixed aqueous solution of 400 g of potassium permanganate and 230 g of potassium hydroxide dissolved in 23000 g of ion-exchanged water was added to give a precipitate; and the precipitate formed was filtered and washed, and the resulting cake was then dried at 120° C. Through these operations, manganese oxide in powder form was obtained. The specific surface area determined using the BET method with nitrogen gas adsorption was 360 m$^2$/g. In the X-ray diffraction pattern in the range of 2θ=10 to 70° obtained for adsorbent A in X-ray diffraction measurement with Cu-Kα radiation, only diffraction peaks indicating α-MnO$_2$ were found. The crystallite size determined for all the diffraction peaks by using the Scherrer equation was in the range of 3 to 5 nm.

Subsequently, a test solution with a pH of 2.8 to 3.2 for a ruthenium ion adsorption test was prepared as follows. Ruthenium (III) chloride n-hydrate, sodium chloride, magnesium chloride hexahydrate, calcium chloride dihydrate and hydrochloric acid were dissolved in ion-exchanged water to prepare an aqueous solution containing 10 ppm of ruthenium ions, 10000 ppm of sodium ions, 500 ppm of magnesium ions and 500 ppm of calcium ions with a pH 2.8 to 3.2.

5.0 mg of adsorbent A was added to 50 mL of the test solution (ruthenium (III) chloride, pH 2.8 to 3.2) at 25° C. under atmospheric pressure, and the resultant was held for 1 hour while being shaked with a shaker at 180 oscillation/min. In the test, a 250 mL plastic container with a lid was used. After the treatment, the entirety of the contents of the plastic container were transferred to a centrifuge tube, and centrifugation was performed for 5 minutes at a rotation frequency of 4000 rpm, and the supernatant was then recovered. The ruthenium concentration in the supernatant thus obtained was measured, and then the ruthenium removal efficiency was calculated.

Example 2

Preparation of Adsorbent B

The adsorbent powder A produced under the conditions in Example 1 was tightly pressed by using a dry high-pressure molding machine (from SINTOKOGIO, LTD., BGL0L001), and further pulverized, and the size of the pulverized product was adjusted with a 35-mesh (500 μm) sieve and a 10-mesh (2000 μm) sieve to prepare a granular adsorbent B with a particle size of 500 to 2000 μm. For 50 ml of the test solution used in Example 1 at 25° C. under atmospheric pressure, 50 mg of adsorbent B was used, and the ruthenium removal efficiency was determined in the same manner as in Example 1.

X-ray photoelectron spectroscopy was performed for adsorbent B before and after the ruthenium adsorption test, and the wide spectrum, Ru 3d XPS spectrum and O 1s XPS spectrum were determined.

Example 3

Preparation of Adsorbent C

The method for preparing adsorbent C was as follows: 900 g of manganese sulfate and 780 g of copper sulfate were dissolved in 2700 g of ion-exchanged water; a mixed aqueous solution of 650 g of potassium permanganate and 950 g of potassium hydroxide dissolved in 2500 g of ion-exchanged water was added to the solution, until the pH of the aqueous solution reached 6 to 7 to give a precipitate; the precipitate formed was filtered and washed, and the resulting cake was then dried at 110° C., where the molar ratio of manganese to copper contained in the oxide of manganese formed was 75:25 (Mn:Cu). The specific surface area measured in the BET method was 220 $m^2/g$, and the shape was a powder. The X-ray diffraction pattern in the range of 2θ=10 to 70° obtained for the adsorbent C in X-ray diffraction measurement with Cu-Kα radiation included two broad peaks, which are characteristic of amorphous materials.

For 50 ml of the test solution used in Example 1 at 25° C. under the atmospheric pressure, 5.0 mg of adsorbent C was used, and the ruthenium removal efficiency was determined in the same manner as in Example 1.

Example 4

Preparation of Adsorbent D

The method for preparing granular adsorbent D using the powder adsorbent C in Example 3 was as follows: the powder adsorbent C was tightly pressed by using the dry high-pressure molding machine (from SINTOKOGIO, LTD., BGL0L001) used in Example 2, and further pulverized, and the size of the pulverized product was adjusted with a 35-mesh (500 μm) sieve and a 10-mesh (2000 μm) sieve to prepare granules with a particle size of 500 to 2000 μm.

For 50 ml of the test solution used in Example 1 at 25° C. under atmospheric pressure, 50 mg of adsorbent D was used, and the ruthenium removal efficiency was determined in the same manner as in Example 1.

Example 5

Preparation of Adsorbent E

The method for preparing adsorbent E was as follows: 700 g of manganese sulfate tetrahydrate was dissolved in 10,000 g of ion-exchanged water heated to 80° C.; a mixed aqueous solution of 400 g of potassium permanganate and 800 g of potassium hydroxide dissolved in 30000 g of ion-exchanged water heated to 80° C. was added to the aqueous solution to give a precipitate; the precipitate formed is filtered and washed, and the resulting cake was then dried at 120° C. Through these operations, massive manganese oxide was obtained. The mass was pulverized to obtain a powder. The specific surface area determined by using the BET method with nitrogen gas adsorption was 350 $m^2/g$. In the X-ray diffraction pattern in the range of 2θ=10 to 70° obtained for adsorbent E in X-ray diffraction measurement with Cu-Kα radiation, only diffraction peaks indicating δ-$MnO_2$ were found.

For 50 ml of the test solution used in Example 1 at 25° C. under atmospheric pressure, 5.0 mg of adsorbent E was used, and the ruthenium removal efficiency was determined in the same manner as in Example 1.

Example 6

Preparation of Adsorbent F

The method for preparing granular adsorbent F was as follows: the massive manganese oxide obtained in the preparation process of Example 5 was pulverized, and the size of the pulverized product was adjusted with a 35-mesh (500 μm) sieve and a 10-mesh (2000 μm) sieve to prepare granules with a particle size of 500 to 20001±m.

For 50 ml of the test solution used in Example 1 at 25° C. under the atmospheric pressure, 50 mg of adsorbent F was used, and the ruthenium removal efficiency was determined in the same manner as in Example 1.

Example 7

Preparation of Adsorbent G

The method for preparing adsorbent G was as follows: the powder of adsorbent A and boehmite alumina (from Sasol Limited, trade name: PURAL SB) were blended together at a weight ratio of 9:1 to prepare a mixed powder; the mixed powder was tightly pressed by using the dry high-pressure molding machine used in Example 2, and further pulverized, and the size of the pulverized product was adjusted with a 35-mesh (500 μm) sieve and a 10-mesh (2000 μm) sieve to prepare granules with a particle size of 500 to 2000 μm.

For 50 ml of the test solution used in Example 1 at 25° C. under atmospheric pressure, 50 mg of the adsorbent G was used, and the ruthenium removal efficiency was determined in the same manner as in Example 1.

Example 8

Preparation of Adsorbent I

The method for preparing adsorbent I was as follows: 4 g of potassium permanganate and 4 ml of ethanol were dissolved in 400 g of ion-exchanged water; the resulting aqueous solution is transferred in an autoclave (from TAIATSU TECHNO CORPORATION, TEM-D-1000M) and held for 24 hours at 150° C.; a precipitate formed was filtered and washed, and the resulting cake was then dried at 350° C. Through these operations, massive manganese oxide was obtained. The mass was pulverized to obtain a powder. The specific surface area determined by using the BET method with nitrogen gas adsorption was 18 $m^2/g$. In the X-ray diffraction pattern in the range of 2θ=10 to 70° obtained for the adsorbent I in X-ray diffraction measurement with Cu-Kα radiation, only diffraction peaks indicating β-$MnO_2$ were found.

For 50 ml of the test solution used in Example 1 at 25° C. under atmospheric pressure, 5.0 mg of the adsorbent I was used, and the ruthenium removal efficiency was determined in the same manner as in Example 1.

Example 9

Preparation of Adsorbent J

The method for preparing adsorbent J was as follows: 2 g of spinel-type lithium manganate (from Sigma-Aldrich Co., LLC., trade name: Lithium manganese oxide) was dispersed in 2,000 g of 0.5 mol/L aqueous solution of hydrochloric acid, and the resultant was stirred for 24 hours; the resulting precipitate was filtered and washed, and then dried under vacuum to obtain a powder. The specific surface area determined by using the BET method with nitrogen gas adsorption was 13 $m^2/g$. In the X-ray diffraction pattern in the range of 2θ=10 to 70° obtained for the adsorbent J in X-ray diffraction measurement with Cu-Kα radiation, only diffraction peaks indicating λ-$MnO_2$ were found.

For 50 ml of the test solution used in Example 1 at 25° C. under the atmospheric pressure, 5.0 mg of adsorbent J was used, and the ruthenium removal efficiency was determined in the same manner as in Example 1.

Example 10

A test solution with a pH of 5.8 to 6.8 for a ruthenium ion adsorption test was prepared as follows. Ruthenium (III) chloride n-hydrate, sodium chloride, magnesium chloride hexahydrate, calcium chloride dihydrate and hydrochloric acid were dissolved in ion-exchanged water to prepare an aqueous solution containing 10 ppm of ruthenium ions, 10000 ppm of sodium ions, 500 ppm of magnesium ions and 500 ppm of calcium ion with a pH of 5.8 to 6.8.

For 50 ml of the test solution (ruthenium (III) chloride, pH 5.8 to 6.8) at 25° C. under atmospheric pressure, 5.0 mg of adsorbent A was used, and the ruthenium removal efficiency was determined in the same manner as in Example 1.

Example 11

For 50 ml of the test solution used in Example 10 at 25° C. under the atmospheric pressure, 5.0 g of adsorbent C was used, and the ruthenium removal efficiency was determined in the same manner as in Example 1.

Example 12

For 50 ml of the test solution used in Example 10 at 25° C. under atmospheric pressure, 5.0 mg of adsorbent E was used, and the ruthenium removal efficiency was determined in the same manner as in Example 1.

Example 13

A test solution for a ruthenium complex ion adsorption test was prepared as follows. Ruthenium (III) nitrosylnitrate, sodium chloride, magnesium chloride hexahydrate, calcium chloride dihydrate and hydrochloric acid were dissolved in ion-exchanged water to prepare an aqueous solution containing 10 ppm of ruthenium complex ions, 10000 ppm of sodium ions, 500 ppm of magnesium ions, and 500 ppm of calcium ions with a pH of 2.8.

For 50 ml of the test solution (ruthenium (III) nitrosylnitrate) at 25° C. under atmospheric pressure, 5.0 mg of adsorbent A was used, and the ruthenium removal efficiency was determined in the same manner as in Example 1.

Example 14

For 50 ml of the test solution used in Example 13 at 25° C. under atmospheric pressure, 5.0 mg of adsorbent C was used, and the ruthenium removal efficiency was determined in the same manner as in Example 1.

Example 15

For 50 ml of the test solution used in Example 13 at 25° C. under atmospheric pressure, 5.0 mg of adsorbent E was used, and the ruthenium removal efficiency was determined in the same manner as in Example 1.

Example 16

A test solution for a ruthenate ion adsorption test was prepared as follows. Potassium ruthenate (VI) was dissolved in ion-exchanged water to prepare an aqueous solution containing 20 ppm of ruthenate ions with a pH of 8.6.

For 50 ml of the test solution (potassium ruthenate (VI)) at 25° C. under atmospheric pressure, 50 mg of adsorbent A was used, and the ruthenium removal efficiency was determined in the same manner as in Example 1.

Example 17

For 50 ml of the test solution used in Example 16 at 25° C. under atmospheric pressure, 50.0 mg of adsorbent C was used, and the ruthenium removal efficiency was determined in the same manner as in Example 1.

Example 18

For 50 ml of the test solution used in Example 16 at 25° C. under atmospheric pressure, 50.0 mg of adsorbent E was used, and the ruthenium removal efficiency was determined in the same manner as in Example 1.

Comparative Example 1

For 50 ml of the test solution used in Example 1 at 25° C. under atmospheric pressure without the addition of any adsorbent, the ruthenium removal efficiency was determined in the same manner as in Example 1.

Reference Example 1

For 50 ml of the test solution used in Example 1 at 25° C. under the atmospheric pressure, 5.0 mg of a reagent of manganese oxide in a powdered state (from Wako Pure Chemical Industries Ltd., trade name: manganese oxide (IV), powder, grade: Wako 1st Grade) was used (adsorbent H), and the ruthenium removal efficiency was determined in the same manner as in Example 1.

In the XRD pattern for adsorbent H (FIG. 1), only diffraction peaks indicating ε-$MnO_2$ and γ-$MnO_2$ were found. The specific surface area measured by the BET method was 50 $m^2/g$.

Comparative Example 2

For 50 ml of the test solution used in Example 10 at 25° C. under atmospheric pressure without the addition of any adsorbent, the ruthenium removal efficiency was determined in the same manner as in Example 1.

Reference Example 2

For 50 ml of the test solution used in Example 10 at 25° C. under atmospheric pressure, 5.0 mg of the adsorbent H was used, and the ruthenium removal efficiency was determined in the same manner as in Example 1.

Comparative Example 3

For 50 ml of the test solution used in Example 13 at 25° C. under the atmospheric pressure without addition of any adsorbent, the ruthenium removal efficiency was determined in the same manner as in Example 1.

Reference Example 3

For 50 ml of the test solution used in Example 13 at 25° C. under atmospheric pressure, 5.0 mg of adsorbent H was used, and the ruthenium removal efficiency was determined in the same manner as in Example 1.

Comparative Example 4

For 50 ml of the test solution used in Example 16 at 25° C. under atmospheric pressure without the addition of any adsorbent, the ruthenium removal efficiency was determined in the same manner as in Example 1.

Reference Example 4

For 50 ml of the test solution used in Example 16 at 25° C. under atmospheric pressure, 50.0 mg of adsorbent H was used, and the ruthenium removal efficiency was determined in the same manner as in Example 1.

The measurement results for Examples 1 to 9, Comparative Example 1 and Reference Example 1 are shown in Table 1 (metals other than manganese contained in an adsorbent (powder) or a shaped adsorbent (granule) are referred to as "additional second metal").

TABLE 1

Measurement results (pH 2.8 to 3.2), aqueous solution of ruthenium (III) chloride

| | Adsorbent | Shape of adsorbent | Additional second metal | Oxide of Mn/oxide of additional second metal; weight ratio*[1] | Specific surface area ($m^2$/g) | Crystal structure | Amount of adsorbent used | Ruthenium removal efficiency |
|---|---|---|---|---|---|---|---|---|
| Example 1 | A | powder | — | 100:0 | 360 | $\alpha$-$MnO_2$ | 5.0 mg | 84% |
| Example 2 | B | granule (500 to 2000 μm) | — | 100:0 | 250 | | 50 mg | 72% |
| Example 3 | C | powder | Cu | 75:25 | 220 | amorphous | 5.0 mg | 96% |
| Example 4 | D | granule (500 to 2000 μm) | Cu | 75:25 | 200 | | 50 mg | 98% |
| Example 5 | E | powder | — | 100:0 | 350 | $\delta$-$MnO_2$ | 5.0 mg | 83% |
| Example 6 | F | granule (500 to 2000 μm) | — | 100.0 | 350 | | 50 mg | 99% |
| Example 7 | G | granule (500 to 2000 μm) | Al | 90:10 | 310 | | 50 mg | 98% |
| Comparative Example 1 | — | without adsorbent | | | | | none | 0% |
| Reference Example 1 | H | powder | | | 50 | coexistence of ε-type $MnO_2$ and γ-type $MnO_2$ | 5.0 mg | 19% |
| Example 8 | I | powder | — | 100:0 | 18 | $\beta$-$MnO_2$ | 5.0 mg | 7% |
| Example 9 | J | powder | — | | 13 | $\lambda$-$MnO_2$ | 5.0 mg | 21% |

*[1]Mn/additional second metal (molar ratio), for Examples 3 and 4

The following statements can be made from Table 1:

1) While the ruthenium removal efficiency of adsorbent H in Reference Example 1, with a specific surface area of 50 m$^2$/g, was 19%, the ruthenium removal efficiency of adsorbent A in Example 1, with a specific surface area of 360 m$^2$/g, was 84%, which was a significantly increased.

2) The reason for 1) can be recognized as being that the specific surface area being a suitable value resulted in a larger number of adsorption sites for ruthenium. For adsorbent A, being α-MnO$_2$, in contrast to adsorbent H, consisting of ε-MnO$_2$ and γ-MnO$_2$, the structure itself may contribute to the increase in the number of adsorption sites for ruthenium to enhance the ruthenium removal efficiency.

3) The ruthenium removal efficiency of adsorbent I, being β-MnO$_2$, in Example 8 was 7%, which was lower than, for example, that in Example 1. α-MnO$_2$, β-MnO$_2$, ε-MnO$_2$ and γ-MnO$_2$ each has a tunnel structure. Such tunnel structures are classified with (m×n), where m is the number of linked MnO$_6$ octahedrons forming the horizontal side of the tunnel, and n is that of those forming the vertical side of the tunnel. α-MnO$_2$ is classified as (2×2), β-MnO$_2$ as (1×1), and γ-MnO$_2$ as coexistence of (1×1) and (1×2). ε-MnO$_2$ has a structure similar to that of γ-MnO$_2$, and includes microtwinning and many structural defects. The tunnel structure in which at least two linked MnO$_6$ octahedrons forming each horizontal and vertical side of the tunnel may contribute to the increase in the number of adsorption sites for ruthenium thereby enhancing the ruthenium removal efficiency.

4) The ruthenium removal efficiency of adsorbent B in Example 2, which was the granulated product of adsorbent A in powder form in Example 1, was lower than that of adsorbent A, even though the amount of use (charged amount) was larger. This is presumably because granulation results in a decrease in the frequency of contact of ruthenium with adsorption sites.

5) Despite the result in which the specific surface area of powder adsorbent C in Example 3, in which copper was allowed to coexist, was smaller than that of adsorbent A containing no copper, the ruthenium removal efficiency of adsorbent C was of a very high value of 96%. This indicates that adsorption of ruthenium depends not only on the specific surface area but also on the nature and number of adsorption sites. Adsorbent C is amorphous. Both the introduction of copper and the amorphous nature of adsorbent C may contribute to the enhancement of the ruthenium removal efficiency.

6) Moreover, in the system with 50 mg of the granular adsorbent consisting of a composite oxide of manganese and copper in Example 4, no decrease in ruthenium removal efficiency from that of the system with 5 mg of a powder (Example 3) was observed. This effect due to granulation is quite different from the effect in the case of adsorbent A, and is very much preferable for the achievement of the combination of simplification of material handling by virtue of granulation and a satisfactory ruthenium removal efficiency. Comparing Example 2 and Example 4 each with the same 50 mg charge, granulation led to a decrease in the ruthenium removal efficiency in cases without copper, and, in contrast, in cases with copper, no decrease in the ruthenium removal efficiency was observed. Although the exact reason is unclear, it is presumably due to the fact that, for example, the copper used as additional transition metal changes a part of the surface of the adsorbent, or facilitates the contact of water to be treated with the granular adsorbent.

7) Powder adsorbent E in Example 5 is classified as δ-MnO$_2$ with a layered structure. The layered structure may also contribute to the increase in the number of adsorption sites for ruthenium, enhancing the ruthenium removal efficiency.

8) The result for Example 7 indicates that granulation of the adsorbent mixed with aluminum oxide also provides a high ruthenium removal efficiency. While granulation of the adsorbent powder with no additive resulted in a decreased specific surface area as in Examples 1 and 2, granulation with mixing with aluminum oxide resulted in an increased specific surface area, and the high ruthenium removal efficiency is expected to reflect the increased specific surface area. Although the reason why the forming of a shaped article after mixing with aluminum oxide results in an increased surface area is unclear, it is presumably because the aluminum oxide functions as a porous binder to facilitate contact of ruthenium with adsorption sites even after granulation.

9) With respect to the crystal structure of the adsorbent, those having a tunnel structure like α-MnO$_2$ in which at least two linked MnO$_6$ octahedrons form each horizontal and vertical side of the tunnel, those which are amorphous, or those having a layered structure are preferable.

10) XPS wide spectra were determined for adsorbent B before and after the experiment to perform qualitative analysis (FIGS. 2 and 3). Comparison thereof revealed that, for the adsorbent after the test, a Ru 3d peak with high intensity appeared at a binding energy of around 280 eV, and thus ruthenium was deposited. While ruthenium (III) chloride n-hydrate was used in the test, the intensity of Cl 2p peak, observed for the adsorbent after the test, at a binding energy of around 200 eV derived from chlorine, was extremely low. From this result, it can be seen that the ruthenium deposited was not ruthenium (III) chloride. The main peaks observed for the adsorbent before the test were those derived from manganese and oxygen. However, the main peaks observed for the adsorbent after the test were those derived from ruthenium and oxygen, which suggests that a ruthenium compound was deposited on the adsorbent. The ruthenium compound deposited was analyzed through determination of XPS spectra for Ru 3d and O 1S (FIGS. 4 and 5). The Ru 3d$_{5/2}$ peaks and the O 1s peak suggest that the trivalent ruthenium used in the test was converted to oxides of tetravalent or higher-valent ruthenium such as RuO$_2$ and RuO$_3$, and adsorbed on the manganese oxide agent. Strong adsorption accompanied by oxidation of ruthenium may enhance the ruthenium removal efficiency.

11) In the above Examples, Comparative Example and Reference Example, non-radioactive ruthenium was used for safety in the experiment. Since non-radioactive ruthenium has the same electronic structure and electronic characteristics as radioactive ruthenium, and ions of non-radioactive ruthenium exhibit adsorption properties similar to those of ions of radioactive ruthenium, it is believed that similar results can be obtained for radioactive ruthenium.

The measurement results for Examples 10 to 12, Comparative Example 2 and Reference Example 2 are shown in Table 2 (metals other than manganese contained in an adsorbent are referred to as "additional second metal").

TABLE 2

Measurement results (pH 5.8 to 6.8), aqueous solution of ruthenium (III) chloride

| | Adsorbent | Shape of adsorbent | Additional second metal | Mn/additional second metal; mole ratio | Specific surface area ($m^2/g$) | Crystal structure | Amount of adsorbent used | Ruthenium removal efficiency |
|---|---|---|---|---|---|---|---|---|
| Example 10 | A | powder | — | 100:0 | 360 | α-$MnO_2$ | 5.0 mg | 96% |
| Example 11 | C | powder | Cu | 75:25 | 220 | amorphous | 5.0 mg | 99% |
| Example 12 | E | powder | — | 100:0 | 350 | δ-$MnO_2$ | 5.0 mg | 98% |
| Comparative Example 2 | — | without adsorbent | | | | | none | 5% |
| Reference Example 2 | H | powder | | | 50 | coexistence of ε-type $MnO_2$ and γ-type $MnO_2$ | 5.0 mg | 83% |

The following statements can be made from Table 2.
1) Adsorbent A in Example 10 exhibited a ruthenium removal efficiency of 96%, adsorbent C in Example 11 exhibited a ruthenium removal efficiency of 99%, and adsorbent E in Example 12 exhibited a ruthenium removal efficiency of 98%. However, the ruthenium removal efficiency of adsorbent H in Reference Example 2 was 83%.

The increase in pH of the solution from 2.8-3.2 to 5.8-6.8 led to higher ruthenium removal efficiencies.
2) Even in cases where the pH of the solution is 5.8 to 6.8, in terms of the crystal structure of the adsorbent, those having a tunnel structure like α-$MnO_2$ in which at least two linked $MnO_6$ octahedrons form each horizontal and vertical side of the tunnel, those which are amorphous or those having a layered structure are preferable.
3) Tables 1 and 2 show the results using an aqueous solution of ruthenium (III) chloride as a test solution, and that extremely high ruthenium removal efficiencies up to 99% were achieved. Ruthenium is expected to be present as a ruthenium cation in aqueous solutions of ruthenium (III) chloride, and it is understood that the adsorbent according to the present invention exhibits extremely high removal performance for ruthenium cations.
4) In the above Examples, Comparative Example and Reference Example, non-radioactive ruthenium was used for safety in the experiment. Since non-radioactive ruthenium has the same electronic structure and electronic characteristics as radioactive ruthenium, and ions of non-radioactive ruthenium exhibit adsorption properties similar to those of ions of radioactive ruthenium, it is believed that similar results can be obtained for radioactive ruthenium.

The measurement results for Examples 13 to 15. Comparative Example 3 and Reference Example 3 are shown in Table 3 (metals other than manganese contained in an adsorbent are referred to as "additional second metal").

TABLE 3

Measurement results (pH 2.8), aqueous solution of ruthenium (III) nitrosylnitrate

| | Adsorbent | Shape of adsorbent | Additional second metal | Mn/additional second metal; mole ratio | Specific surface area ($m^2/g$) | Crystal structure | Amount of adsorbent used | Ruthenium removal efficiency |
|---|---|---|---|---|---|---|---|---|
| Example 13 | A | powder | — | 100:0 | 360 | α-$MnO_2$ | 5.0 mg | 39% |
| Example 14 | C | powder | Cu | 75:25 | 220 | amorphous | 5.0 mg | 54% |
| Example 15 | E | powder | — | 100:0 | 350 | δ-$MnO_2$ | 5.0 mg | 34% |
| Comparative Example 3 | — | without adsorbent | | | | | none | 0% |
| Reference Example 3 | H | powder | | | 50 | coexistence of ε-type $MnO_2$ and γ-type $MnO_2$ | 5.0 mg | 6% |

The following statements can be made from Table 3.
1) The adsorbent according to the present invention, especially, the adsorbent containing transition metals such as copper, as in Example 14, exhibited a ruthenium removal efficiency of about 54%. However, the ruthenium removal efficiency of adsorbent H in Reference Example 3 was 6%. Although the ruthenium removal efficiencies were somewhat lower than those for ruthenium cations in Tables 1 and 2, the results demonstrate the effectiveness of the adsorbent according to the present invention.
2) Adsorbent A in Example 13 exhibited a ruthenium removal efficiency of 39%, adsorbent C in Example 14 exhibited a ruthenium removal efficiency of 54%, and adsorbent E in Example 15 exhibited a ruthenium removal efficiency of 34%. However, the ruthenium removal efficiency of adsorbent H in Reference Example 3 was 6%. In terms of the crystal structure of the adsorbent, also in the case of adsorption treatment for ruthenium (III) nitrosylnitrate, adsorbents having a tunnel structure as α-$MnO_2$ in which at least two linked $MnO_6$ octahedrons form each horizontal and vertical side of the tunnel, those which are amorphous, and those having a layered structure are preferable.

3) In the above Examples, Comparative Example and Reference Example, non-radioactive ruthenium was used for safety in the experiment. Since non-radioactive ruthenium has the same electronic structure and electronic characteristics as radioactive ruthenium, and ions of non-radioactive ruthenium exhibit adsorption properties similar to those of ions of radioactive ruthenium, it is believed that the similar results can be obtained for radioactive ruthenium.

From the results in Tables 1 to 3, it can be concluded that an adsorbent comprising manganese oxide having, as the crystal structure, a tunnel structure like α-$MnO_2$ in which at least two linked $MnO_6$ octahedrons form each horizontal and vertical side of the tunnel, manganese oxide being amorphous or manganese oxide having a layered structure can remove ruthenium at a higher efficiency than manganese oxide with other structures. Regardless of the type of adsorbent, the ruthenium removal efficiencies for ruthenium complex ions using of ruthenium (III) nitrosylnitrate were lower than those for ruthenium cations in using of ruthenium (III) chloride. The lower ruthenium removal efficiencies for ruthenium complex ions are presumably due to the adsorption properties of a ruthenium complex ion, as ruthenium (III) nitrosylnitrate, to the surface of an adsorbent varying depending on the type of the ligand, or because oxidation of ruthenium is less likely to occur under the influence of the ligand.

The measurement results for Examples 16 to 18, Comparative Example 4 and Reference Example 4 are shown in Table 4 (metals other than manganese contained in an adsorbent are referred to as "additional second metal").

of manganese oxide on the ruthenium removal efficiency for potassium ruthenate is unclear, in contrast to the cases using ruthenium (III) chloride and ruthenium (III) nitrosylnitrate. The ruthenium removal efficiency for potassium ruthenate may be higher as the specific surface area Is larger.

4) In the above Examples, Comparative Example and Reference Example, non-radioactive ruthenium was used for safety in the experiment. Since non-radioactive ruthenium has the same electronic structure and electronic characteristics as radioactive ruthenium, and ions of non-radioactive ruthenium exhibit adsorption properties similar to those of ions of radioactive ruthenium, it is believed that similar results can be obtained for radioactive ruthenium.

The invention claimed is:

1. A ruthenium adsorbent comprising manganese oxides as the primary component of the adsorbent, provided that manganese oxides consisting of ε-$MnO_2$ and/or γ-$MnO_2$ are excluded from the manganese oxides,
    wherein the manganese oxides have an amorphous structure or a layered structure or a tunnel structure, and
    wherein, in the case that the manganese oxides have a tunnel structure, the adsorbent comprises an oxide of manganese having at least two linked $MnO_6$ octahedrons forming each horizontal and vertical side of the tunnel structure.

2. The ruthenium adsorbent according to claim 1, wherein the manganese oxides have an amorphous structure and/or α-$MnO_2$ and/or δ-$MnO_2$.

TABLE 4

Measurement results (pH 8.6), aqueous solution of potassium ruthenate (VI)

| | Adsorbent | Shape of adsorbent | Additional second metal | Mn/additional second metal; mole ratio | Specific surface area ($m^2$/g) | Crystal structure | Amount of adsorbent used | Ruthenium removal efficiency |
|---|---|---|---|---|---|---|---|---|
| Example 16 | A | powder | — | 100:0 | 360 | α-$MnO_2$ | 50.0 mg | 79% |
| Example 17 | C | powder | Cu | 75:25 | 220 | amorphous | 50.0 mg | 65% |
| Example 18 | E | powder | — | 100:0 | 350 | δ-$MnO_2$ | 50.0 mg | 70% |
| Comparative Example 4 | — | without adsorbent | | | — | | none | 4% |
| Reference Example 4 | H | powder | | | 50 | coexistence of ε-type $MnO_2$ and γ-type $MnO_2$ | 50.0 mg | 57% |

The following statements can be made from Table 4.

1) Adsorbent A in Example 16 exhibited a high ruthenium removal efficiency of 79%, which indicates high capacity for practical use. Adsorbent C in Example 17 exhibited a ruthenium removal efficiency of 65%, and adsorbent E in Example 18 exhibited a ruthenium removal efficiency of 70%. However, the ruthenium removal efficiency of adsorbent H in Reference Example 4 was 57%.

2) The difference between the ruthenium removal efficiency of each adsorbent according to the present invention and that of adsorbent H in Table 4 was smaller than that in Tables 1 to 3.

3) Since the ruthenium contained in potassium ruthenate (VI) is hexavalent, the adsorbent is expected to adsorb potassium ruthenate by a different mechanism from that of the adsorption accompanied by oxidation, which is expected for ruthenium (III) chloride and ruthenium (III) nitrosylnitrate. Probably because of this, the influence of the structure 3. The ruthenium adsorbent according to claim 1, wherein the manganese oxides have an amorphous structure and/or α-$MnO_2$.

4. The ruthenium adsorbent according to claim 1, wherein a content of manganese calculated as manganese dioxide is 50 parts by weight or more, based on 100 parts by weight of the adsorbent.

5. The ruthenium adsorbent according to claim 1, further comprising at least one additional transition metal element other than manganese.

6. The ruthenium adsorbent according to claim 5, wherein the at least one additional transition metal element is in the form of oxides thereof.

7. The ruthenium adsorbent according to claim 6, wherein the manganese and the at least one additional transition metal element are present in the form of a physical mixture of manganese oxides and oxides of the at least one additional transition metal element.

8. The ruthenium adsorbent according to claim 6, wherein manganese and the at least one additional transition metal element are present in the form of composite oxides thereof.

9. The ruthenium adsorbent according to claim 7, wherein a weight ratio of manganese oxides to oxides of the at least one additional transition metal is 1:0.001 to 1:1, when the weight of the manganese oxides is calculated as the weight of manganese dioxide.

10. The ruthenium adsorbent according to claim 8, wherein the molar ratio of manganese to the at least one additional transition metal element is 1:0.001 to 1:1.

11. The ruthenium adsorbent according to claim 5, wherein the at least one additional transition metal element is selected from the group consisting of iron, cobalt, copper and zinc.

12. The ruthenium adsorbent according to claim 1, having a specific surface area of 70 to 700 $m^2/g$.

13. The ruthenium adsorbent according to claim 1, in the form of a powder.

14. The ruthenium adsorbent according to claim 1, in the form of a shaped article.

15. The ruthenium adsorbent according to claim 1, further comprising an inorganic binder which comprises a metal element other than transition metals and/or a metalloid element.

16. The ruthenium adsorbent according to claim 15, wherein the inorganic binder comprises aluminum oxides or silicon oxides.

17. A method for recovering ruthenium from waste fluid discharged from a production line for industrial products and/or a recycling process for industrial products, comprising contacting the waste fluid with the ruthenium adsorbent according to claim 1, wherein the waste fluid contains ruthenium.

18. A method of removing ruthenium from a ruthenium-containing aqueous solution, comprising the steps of contacting the ruthenium-containing water with the ruthenium adsorbent according to claim 1.

19. The method according to claim 18, wherein the aqueous solution comprises ruthenium in the form of a ruthenium cation, and/or a ruthenium complex ion and/or a ruthenate ion.

20. The method according to claim 18, wherein the ruthenium-containing aqueous solution comprises radioactive ruthenium.

21. The method according to claim 18, wherein the ruthenium-containing aqueous solution comprises sea water and/or water containing an ion selected from the group consisting of a sodium ion, a magnesium ion, a calcium ion, a chlorine ion and other ions, and wherein the aqueous solution further comprises a radioactive element including radioactive ruthenium.

* * * * *